(12) United States Patent  (10) Patent No.: US 8,246,539 B2
Hjelle et al.  (45) Date of Patent: Aug. 21, 2012

(54) PERICARDIUM MANAGEMENT METHOD FOR INTRA-PERICARDIAL SURGICAL PROCEDURES

(75) Inventors: Aaron J. Hjelle, Champlin, MN (US); Paul Andrew Pignato, Stacy, MN (US); Robert G. Walsh, Lakeville, MN (US); Richard C. Mattison, Zimmerman, MN (US)

(73) Assignee: Mardil, Inc., Plymouth, MN (US)

( * ) Notice: Subject to any disclaimer, the term of this patent is extended or adjusted under 35 U.S.C. 154(b) by 0 days.

(21) Appl. No.: 12/715,931

(22) Filed: Mar. 2, 2010

(65) Prior Publication Data

US 2010/0152542 A1 Jun. 17, 2010

Related U.S. Application Data

(63) Continuation of application No. 11/437,842, filed on May 19, 2006, now abandoned.

(51) Int. Cl.
*A61B 1/32* (2006.01)
(52) U.S. Cl. .......... 600/208; 600/203; 600/206
(58) Field of Classification Search .......... 600/203, 600/206, 208
See application file for complete search history.

(56) References Cited

U.S. PATENT DOCUMENTS

| | | | |
|---|---|---|---|
| 1,682,119 A | 8/1928 | Field | |
| 1,965,542 A | 11/1933 | Colvin, Jr. | |
| 1,982,207 A | 11/1934 | Furniss | |
| 2,138,603 A | 11/1938 | Johnson | |
| 2,278,926 A | 4/1942 | Hartwell | |
| 2,376,442 A | 5/1945 | Mehler | |
| 2,992,550 A | 7/1961 | Frith | |
| 3,384,530 A | 5/1968 | Mercer et al. | |
| 3,452,742 A | 7/1969 | Muller | |
| 3,551,543 A | 12/1970 | Mercer et al. | |
| 3,587,567 A | 6/1971 | Schiff | |
| 3,732,662 A | 5/1973 | Paxton | |
| 3,768,643 A | 10/1973 | Bruno | |
| 3,782,370 A * | 1/1974 | McDonald | 600/207 |
| 3,983,863 A | 10/1976 | Janke et al. | |
| 4,048,990 A | 9/1977 | Goetz | |

(Continued)

FOREIGN PATENT DOCUMENTS

DE 3 24 524 8/1920

(Continued)

OTHER PUBLICATIONS

International Search Report and Written Opinion issued in PCT/US07/12032, mailed Aug. 20, 2008, 9 pages.

(Continued)

*Primary Examiner* — Eduardo C Robert
*Assistant Examiner* — Stuart S Bray
(74) *Attorney, Agent, or Firm* — Gordon & Rees LLP; Laurie A. Axford; David R. Heckadon

(57) ABSTRACT

A method for managing the pericardium during intra-pericardial procedures such as the delivery of cardiac support devices. One embodiment of the method includes making an incision through the pericardium to provide access to the pericardial space, and inserting a plurality of strips of lubricious material into and through the incision. The strips of material are spaced around the edges of the incision to form a tubular barrier against the pericardium. End portions of the strips of material in the pericardial space are expanded away from the body to form a lip that lines the inside of the pericardium around the incision.

8 Claims, 15 Drawing Sheets

U.S. PATENT DOCUMENTS

| | | | |
|---|---|---|---|
| 4,196,534 A | 4/1980 | Shibamoto | |
| 4,403,604 A | 9/1983 | Wilkinson et al. | |
| 4,421,107 A * | 12/1983 | Estes et al. | 600/206 |
| 4,428,375 A | 1/1984 | Ellman | |
| 4,466,331 A | 8/1984 | Matheson | |
| 4,536,893 A | 8/1985 | Parravicini | |
| 4,567,900 A | 2/1986 | Moore | |
| 4,630,597 A | 12/1986 | Kantrowitz et al. | |
| 4,637,377 A | 1/1987 | Loop | |
| 4,690,134 A | 9/1987 | Snyders | |
| 4,790,850 A | 12/1988 | Dunn et al. | |
| 4,821,723 A | 4/1989 | Baker, Jr. et al. | |
| 4,827,932 A | 5/1989 | Ideker et al. | |
| 4,834,707 A | 5/1989 | Evans | |
| 4,840,626 A | 6/1989 | Linsky et al. | |
| 4,878,890 A | 11/1989 | Bilweis | |
| 4,932,972 A | 6/1990 | Dunn et al. | |
| 4,936,857 A | 6/1990 | Kulik | |
| 4,957,477 A | 9/1990 | Lundback | |
| 4,973,300 A | 11/1990 | Wright | |
| 4,976,730 A | 12/1990 | Kwan-Gett | |
| 4,995,857 A | 2/1991 | Arnold | |
| 5,042,463 A | 8/1991 | Lekholm | |
| 5,057,117 A | 10/1991 | Atweh | |
| 5,074,129 A | 12/1991 | Matthew | |
| 5,087,243 A | 2/1992 | Avitall | |
| 5,131,905 A | 7/1992 | Grooters | |
| 5,150,706 A | 9/1992 | Cox et al. | |
| 5,186,711 A | 2/1993 | Epstein | |
| 5,188,813 A | 2/1993 | Fairey et al. | |
| 5,192,314 A | 3/1993 | Daskalakis | |
| 5,207,725 A | 5/1993 | Pinkerton | |
| 5,224,363 A | 7/1993 | Sutton | |
| 5,231,974 A * | 8/1993 | Giglio et al. | 600/206 |
| 5,256,132 A | 10/1993 | Snyders | |
| 5,279,539 A * | 1/1994 | Bohan et al. | 600/37 |
| 5,290,217 A | 3/1994 | Campos | |
| 5,336,253 A | 8/1994 | Gordon et al. | |
| 5,339,657 A | 8/1994 | McMurray | |
| 5,341,815 A | 8/1994 | Cofone et al. | |
| 5,356,432 A | 10/1994 | Rutkow et al. | |
| 5,366,460 A | 11/1994 | Eberbach | |
| 5,383,840 A | 1/1995 | Heilman et al. | |
| 5,385,156 A | 1/1995 | Oliva | |
| 5,405,360 A | 4/1995 | Tovey | |
| 5,409,703 A | 4/1995 | McAnalley et al. | |
| 5,429,584 A | 7/1995 | Chiu | |
| 5,507,779 A | 4/1996 | Altman | |
| 5,520,610 A * | 5/1996 | Giglio et al. | 600/233 |
| 5,522,790 A * | 6/1996 | Moll et al. | 600/204 |
| 5,524,633 A * | 6/1996 | Heaven et al. | 600/562 |
| 5,533,958 A | 7/1996 | Wilk | |
| 5,558,617 A | 9/1996 | Heilman et al. | |
| 5,593,441 A | 1/1997 | Lichtenstein et al. | |
| 5,603,337 A | 2/1997 | Jarvik | |
| 5,611,515 A | 3/1997 | Benderev et al. | |
| 5,647,380 A | 7/1997 | Campbell et al. | |
| 5,688,223 A * | 11/1997 | Rosendahl | 600/215 |
| 5,695,525 A | 12/1997 | Mulhauser et al. | |
| 5,702,343 A | 12/1997 | Alferness | |
| 5,713,954 A | 2/1998 | Rosenberg et al. | |
| 5,735,290 A | 4/1998 | Sterman et al. | |
| 5,766,216 A | 6/1998 | Gangal et al. | |
| 5,782,746 A | 7/1998 | Wright | |
| 5,800,334 A | 9/1998 | Wilk | |
| 5,800,528 A | 9/1998 | Lederman et al. | |
| 5,839,842 A | 11/1998 | Wanat et al. | |
| 5,853,422 A | 12/1998 | Huebsch et al. | |
| 5,928,250 A | 7/1999 | Koike et al. | |
| 5,931,810 A | 8/1999 | Grabek | |
| 5,961,440 A | 10/1999 | Schweich, Jr. et al. | |
| 5,972,013 A | 10/1999 | Schmidt | |
| 5,980,455 A * | 11/1999 | Daniel et al. | 600/235 |
| 5,990,378 A | 11/1999 | Ellis | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,076,013 A | 6/2000 | Brennan et al. | |
| 6,077,214 A | 6/2000 | Mortier et al. | |
| 6,077,218 A | 6/2000 | Alferness | |
| 6,085,754 A | 7/2000 | Alferness et al. | |
| 6,089,051 A | 7/2000 | Gorywoda et al. | |
| 6,095,968 A | 8/2000 | Snyders | |
| 6,123,662 A | 9/2000 | Alferness et al. | |
| 6,126,590 A | 10/2000 | Alferness | |
| 6,142,935 A | 11/2000 | Flom et al. | |
| 6,142,936 A | 11/2000 | Beane et al. | |
| 6,155,968 A | 12/2000 | Wilk | |
| 6,155,972 A | 12/2000 | Nauertz et al. | |
| 6,165,121 A | 12/2000 | Alferness | |
| 6,165,122 A | 12/2000 | Alferness | |
| 6,169,922 B1 | 1/2001 | Alferness et al. | |
| 6,174,279 B1 | 1/2001 | Girard | |
| 6,179,791 B1 | 1/2001 | Krueger | |
| 6,193,648 B1 | 2/2001 | Krueger | |
| 6,205,747 B1 | 3/2001 | Paniagua Olaechea | |
| 6,206,004 B1 | 3/2001 | Schmidt et al. | |
| 6,224,540 B1 | 5/2001 | Lederman et al. | |
| 6,230,714 B1 | 5/2001 | Alferness et al. | |
| 6,241,654 B1 | 6/2001 | Alferness | |
| 6,254,534 B1 | 7/2001 | Butler et al. | |
| 6,293,906 B1 | 9/2001 | Vanden Hoek et al. | |
| 6,360,749 B1 | 3/2002 | Jayaraman | |
| 6,370,429 B1 | 4/2002 | Alferness et al. | |
| 6,375,608 B1 | 4/2002 | Alferness | |
| 6,382,211 B1 | 5/2002 | Crook | |
| 6,402,680 B2 | 6/2002 | Mortier et al. | |
| 6,416,459 B1 | 7/2002 | Haindl | |
| 6,425,856 B1 | 7/2002 | Shapland et al. | |
| 6,432,039 B1 | 8/2002 | Wardle | |
| 6,440,063 B1 | 8/2002 | Beane et al. | |
| 6,450,983 B1 | 9/2002 | Rambo | |
| 6,482,146 B1 | 11/2002 | Alferness et al. | |
| 6,508,756 B1 | 1/2003 | Kung et al. | |
| 6,517,570 B1 | 2/2003 | Lau et al. | |
| 6,537,203 B1 | 3/2003 | Alferness et al. | |
| 6,537,284 B1 * | 3/2003 | Inoue | 606/108 |
| 6,541,678 B2 | 4/2003 | Klein | |
| 6,544,168 B2 | 4/2003 | Alferness | |
| 6,564,094 B2 | 5/2003 | Alferness et al. | |
| 6,567,699 B2 | 5/2003 | Alferness et al. | |
| 6,569,082 B1 | 5/2003 | Chin | |
| 6,572,533 B1 | 6/2003 | Shapland et al. | |
| 6,579,226 B2 | 6/2003 | Vanden Hoek et al. | |
| 6,582,355 B2 | 6/2003 | Alferness et al. | |
| 6,587,734 B2 | 7/2003 | Okuzumi | |
| 6,602,184 B2 | 8/2003 | Lau et al. | |
| 6,612,978 B2 | 9/2003 | Lau et al. | |
| 6,612,979 B2 | 9/2003 | Lau et al. | |
| 6,613,952 B2 | 9/2003 | Rambo | |
| 6,645,139 B2 | 11/2003 | Haindl | |
| 6,663,558 B2 | 12/2003 | Lau et al. | |
| 6,673,009 B1 | 1/2004 | Vanden Hoek et al. | |
| 6,682,474 B2 | 1/2004 | Lau et al. | |
| 6,682,475 B2 | 1/2004 | Cox et al. | |
| 6,682,476 B2 | 1/2004 | Alferness et al. | |
| 6,689,048 B2 | 2/2004 | Vanden Hoek et al. | |
| 6,695,769 B2 | 2/2004 | French et al. | |
| 6,702,732 B1 | 3/2004 | Lau et al. | |
| 6,723,041 B2 | 4/2004 | Lau et al. | |
| 6,723,044 B2 | 4/2004 | Pulford et al. | |
| 6,730,016 B1 | 5/2004 | Cox et al. | |
| 6,755,779 B2 | 6/2004 | Vanden Hoek et al. | |
| 6,881,185 B2 | 4/2005 | Vanden Hoek et al. | |
| 6,893,392 B2 | 5/2005 | Alferness | |
| 6,902,522 B1 | 6/2005 | Walsh et al. | |
| 6,902,524 B2 | 6/2005 | Alferness et al. | |
| 6,908,426 B2 | 6/2005 | Shapland et al. | |
| 6,939,296 B2 | 9/2005 | Ewers et al. | |
| 6,951,534 B2 | 10/2005 | Girard | |
| 7,033,319 B2 | 4/2006 | Pulford et al. | |
| 7,060,023 B2 | 6/2006 | French et al. | |
| 7,081,086 B2 | 7/2006 | Lau et al. | |
| 7,155,295 B2 | 12/2006 | Lau et al. | |
| 7,163,507 B2 | 1/2007 | Alferness et al. | |
| 7,189,203 B2 | 3/2007 | Lau et al. | |
| 7,235,042 B2 | 6/2007 | Vanden Hoek et al. | |

| | | | |
|---|---|---|---|
| 7,238,154 B2 * | 7/2007 | Ewers et al. | 600/208 |
| 7,252,632 B2 | 8/2007 | Shapland et al. | |
| 7,398,781 B1 | 7/2008 | Chin | |
| 7,537,564 B2 * | 5/2009 | Bonadio et al. | 600/208 |
| 7,909,761 B2 * | 3/2011 | Banchieri et al. | 600/208 |
| 2002/0019580 A1 | 2/2002 | Lau et al. | |
| 2003/0078478 A1 * | 4/2003 | Bonadio et al. | 600/208 |
| 2003/0229260 A1 | 12/2003 | Girard et al. | |
| 2004/0049099 A1 * | 3/2004 | Ewers et al. | 600/206 |
| 2004/0059181 A1 | 3/2004 | Alferness | |
| 2005/0033109 A1 | 2/2005 | Lau et al. | |
| 2005/0059854 A1 | 3/2005 | Vanden Hoek et al. | |
| 2005/0059855 A1 | 3/2005 | Lau et al. | |
| 2005/0059865 A1 | 3/2005 | Kahle et al. | |
| 2005/0090707 A1 | 4/2005 | Lau et al. | |
| 2005/0171589 A1 | 8/2005 | Lau et al. | |
| 2005/0192474 A1 | 9/2005 | Vanden Hoek et al. | |
| 2005/0241647 A1 | 11/2005 | Nguyen et al. | |
| 2005/0256368 A1 | 11/2005 | Klenk et al. | |
| 2005/0283050 A1 * | 12/2005 | Gundlapalli et al. | 600/208 |
| 2005/0288558 A1 * | 12/2005 | Ewers et al. | 600/206 |
| 2005/0288715 A1 | 12/2005 | Lau et al. | |
| 2006/0009831 A1 | 1/2006 | Lau et al. | |
| 2006/0229490 A1 | 10/2006 | Chin | |
| 2006/0270896 A1 | 11/2006 | Dietz et al. | |
| 2007/0208211 A1 | 9/2007 | Alferness et al. | |
| 2007/0219407 A1 | 9/2007 | Vanden Hoek et al. | |
| 2007/0225547 A1 | 9/2007 | Alferness et al. | |
| 2007/0225569 A1 * | 9/2007 | Ewers et al. | 600/206 |
| 2008/0033421 A1 * | 2/2008 | Davis et al. | 606/28 |
| 2008/0097163 A1 * | 4/2008 | Butler et al. | 600/208 |

FOREIGN PATENT DOCUMENTS

| | | |
|---|---|---|
| DE | 38 31 540 | 4/1989 |
| DE | 295 17 393 | 3/1996 |
| EP | 0 280 564 | 8/1988 |
| EP | 0 303 719 | 2/1989 |
| EP | 0 557 964 | 9/1993 |
| GB | 2 209 678 | 5/1989 |
| JP | 60-203250 | 10/1985 |
| JP | 01-145066 | 6/1989 |
| JP | 2-271829 | 11/1990 |
| SU | 1009457 | 4/1983 |
| WO | WO 93/03685 | 3/1993 |
| WO | WO 96/16601 | 6/1996 |
| WO | WO 96/31175 | 10/1996 |
| WO | WO 98/14136 | 4/1998 |
| WO | WO 98/29041 | 7/1998 |
| WO | WO 98/35632 | 8/1998 |
| WO | WO 98/58598 | 12/1998 |
| WO | WO 99/44534 | 9/1999 |
| WO | WO 00/02500 | 1/2000 |
| WO | WO 00/06026 | 2/2000 |
| WO | WO 00/06027 | 2/2000 |
| WO | WO 00/06028 | 2/2000 |
| WO | WO 00/16700 | 3/2000 |
| WO | WO 01/02500 | 1/2001 |
| WO | WO 01/26559 | 4/2001 |
| WO | WO 01/67985 | 9/2001 |
| WO | WO 2006/023580 | 3/2006 |

OTHER PUBLICATIONS

"Abstracts From the 68th Scientific Sessions, Anaheim Convention Center, Anaheim, California, Nov. 13-16, 1995", *American Heart Association Supplement to Circulation*, vol. 92, No. 8, Abstracts 1810-1813 (Oct. 15, 1995).

Capomolla et al., "Dobutamine and nitroprusside infusion in patients with severe congestive heart failure: Hemodynamic improvement by discordant effects on mitral regurgitation, left atrial function, and ventricular function", *American Heart Journal*, pp. 1089-1098 (Dec. 1997).

Capouya et al., "Girdling Effect of Nonstimulated Cardiomyoplasty on Left Ventricular Function", *The Society of Thoracic Surgeons*, vol. 56, pp. 867-871 (1993).

Cohn, "The Management of Chronic Heart Failure", *The New England Journal of Medicine*, vol. 335, No. 7, pp. 490-498 (Aug. 15, 1996).

Colleta et al., "Prognostic value of left ventricular volume response during dobutamine stress echocardiography", *European Heart Journal*, vol. 18, pp. 1599-1605 (Oct. 1997).

deVries, G. et al., "A Novel Technique for Measurement of Pericardial Balloon," *Am. J. Physiol Heart Circ Physiol*, vol. 280, No. 6, pp. H2815-H2822 (Jan. 2001).

Guasp, "Una protesis contentiva para el tratamiento de la miocardiopatia dilatada" *Revista Espanola de Cardiologia*, vol. 51, No. 7, pp. 521-528 (1998). (Includes the English translation).

Hamilton, D. et al., "Static and Dynamic Operating Characteristics of a Pericardial Balloon," *J. Appl. Physiol.*, vol. 90, No. 4, pp. 1481-1488 (Apr. 2001).

Kass et al., "Reverse Remodeling From Cardiomyoplasty in Human Heart Failure", *Circulation*, vol. 91, No. 9, pp. 2314-2318 (May 1, 1995).

Labrousse, et al., "Implantation of a Cardiac Support Device by the 'Parachute-Like' Technique through Sternal and Trans-Abdominal Approach", *Hopital Haut Bordeaux University Hospital, France; Lenox Hill Hospital New York, United States*.

Levin et al., "Reversal of Chronic Ventricular Dilation in Patients With End-Stage Cardiomyopathy by Prolonged Mechanical Unloading", *Circulation*, vol. 91, No. 11, pp. 2717-2720 (Jun. 1, 1995).

Oh et al., "The Effects of Prosthetic Cardiac Binding and Adynamic Cardiomyoplasty in a Model of Dilated Cardiomyopathy", *The Journal of Thoracic and Cardiovascular Surgery*, vol. 116, No. 1, pp. 148-153 (Jul. 1998).

Paling, "Two-Bar Fabrics (Part-Set Threading)", *Warp Knitting Technology*, Columbine Press (Publishers) Ltd., Buxton, Great Britain, p. 111 (1970).

Vaynblat et al., "Cardiac Binding in Experimental Heart Failure", *Ann Thorac Surg*, vol. 64 (1997).

Vinereanu, et al., "Worsening Global Diastolic Dysfunction of the Left Ventricle is Associated with a Progressive Decline in Longitudinal Systolic Function", *European Journal of Heart Failure*, Aug. 7(5): 820-8 (2005).

U.S. Appl. No. 60/148,130 entitled, "Apparatus and Method for Endoscopic Pericardial Access", filed Aug. 10, 1999.

U.S. Appl. No. 60/150,737 entitled, "Longitudinal Mechanical Dilator for Vessel Harvesting", filed Aug. 25, 1999.

U.S. Appl. No. 09/635,345 entitled, "Apparatus and Methods for Subxiphoid Endoscopic Access", filed Aug. 9, 2000.

Supplemental European Search Report issued in EP 07809118, mailed Dec. 4, 2009, 10 pages.

\* cited by examiner

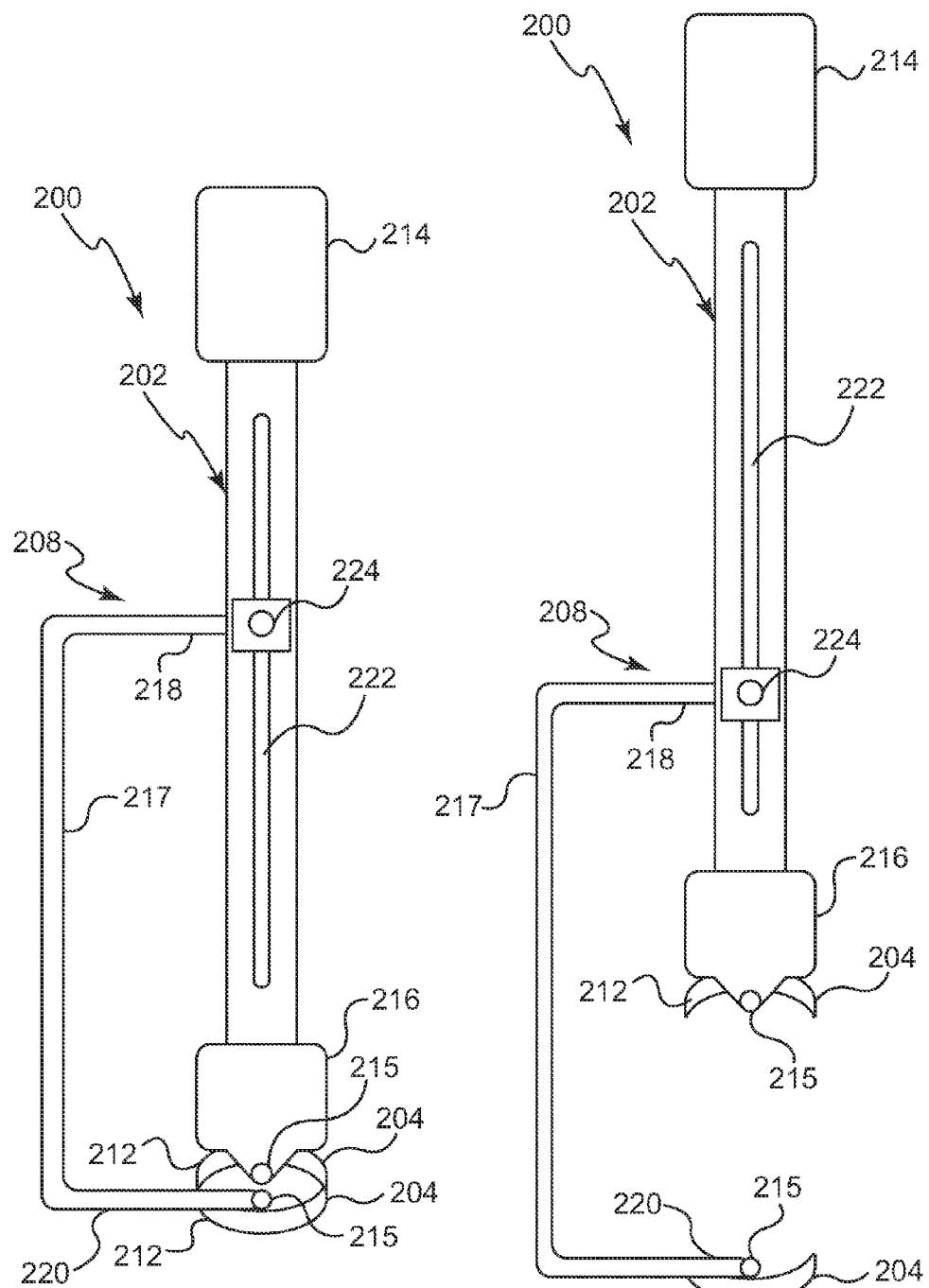

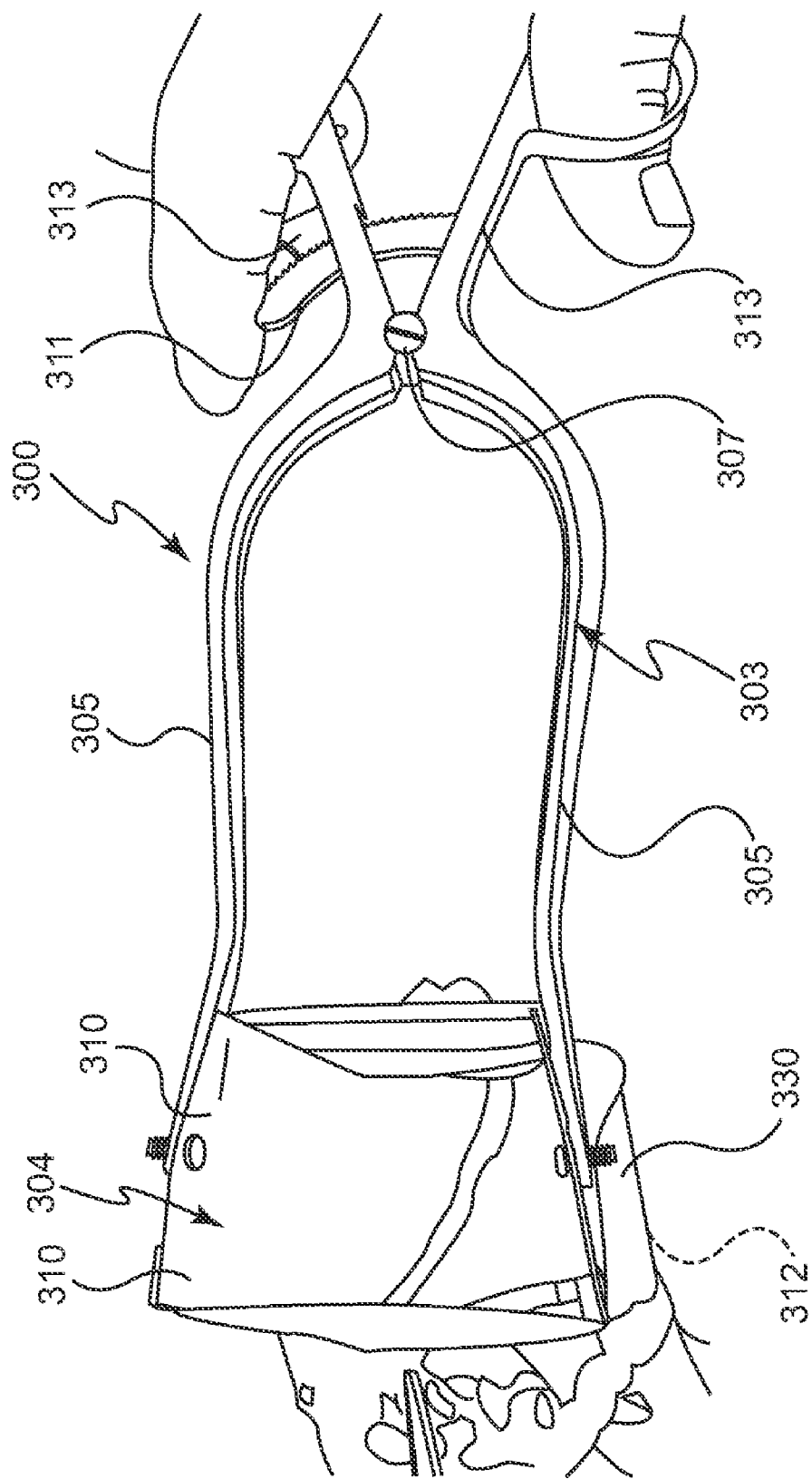

PERICARDIUM MANAGEMENT METHOD FOR INTRA-PERICARDIAL SURGICAL PROCEDURES

CROSS-REFERENCE TO RELATED APPLICATION

This application is a continuation of U.S. patent application Ser. No. 11/437,842, filed May 19, 2006, entitled PERICARDIUM MANAGEMENT METHOD FOR INTRA-PERICARDIAL SURGICAL PROCEDURES, which application is incorporated herein by reference in its entirety and for all purposes.

FIELD OF THE INVENTION

The invention is a method for manipulating the pericardium during surgical or other procedures requiring access to the pericardial space.

BACKGROUND OF THE INVENTION

The pericardium is a multi-layer membranous fibro serous sac that surrounds the heart. An inner layer of the pericardium, known as the serous pericardium, is adjacent to the outer layer of the heart, also known as the epicardium. An outer layer of the pericardium is known as the fibrous pericardium. Between the fibrous pericardium and serous pericardium is a space known as the pericardial space. The term "pericardium" is often used, however, to refer only to the fibrous pericardium. Similarly, the term "pericardial space" is often used to refer generally to the space between the fibrous pericardium and the heart.

Certain surgical or other procedures on the heart require access to the pericardial space through the pericardium. Known approaches for accessing the pericardium and heart from outside the body include sternotomy and sub-xyphoid approaches. One such surgical procedure that requires access to the pericardial space is the delivery of cardiac support devices. Cardiac support devices are structures, sometimes referred to as jackets, that surround all or portions of a diseased heart. These devices are intended to treat chronic heart failure or other cardiac disease, which may be associated valvular dysfunction, by constraining expansion of the heart. They can be delivered and implanted using conventional cardiothoracic surgical techniques or minimally invasive surgical procedures. Devices of these types and associated delivery tools and methods are shown, for example, in the following U.S. patents, all of which are incorporated herein by reference in their entirety.

| Inventor Name | Patent/Publication No. |
| --- | --- |
| Alferness | 5,702,343 |
| Alferness et al. | 6,123,662 |
| Vanden Hoek et al. | 6,293,906 |
| Alferness et al. | 6,482,146 |
| Lau et al. | 6,702,732 |
| Walsh et al. | 6,902,522 |
| Girard et al. | 6,951,534 |

Tools and methods for accessing the pericardial space and for introducing other instruments and therapeutic devices such as cardiac support devices into that space are also known. Examples of tools and methods of these types are shown in the following U.S. patents and published applications, all of which are incorporated herein by reference in their entirety.

| Inventor Name | Patent/Publication No. |
| --- | --- |
| Grabek | 5,931,810 |
| Schmidt | 5,972,013 |
| Schmidt et al. | 6,206,004 |
| Lau et al. | 2005/0055032 |
| Lau et al. | 2005/0102010 |

Cardiac support devices of the type described above are typically delivered through an incision in the pericardium near the apex of the heart. Visualizing the heart and mounting the devices through the incision can involve moving the incision and manipulating the pericardium. In the course of these procedures the pericardium can sometimes interfere with the delivery of the device.

There is, therefore, a continuing need for improved devices and methods for managing the pericardium during intra-pericardial procedures. Devices and methods that can enhance cardiac support device delivery procedures would be especially desirable.

SUMMARY OF THE INVENTION

The present invention is an improved method for managing a patient's pericardium during intra-pericardial procedures. The efficiency of procedures such as the delivery of cardiac support devices can be greatly enhanced by the method.

One embodiment of the invention includes making an incision though the pericardium to provide access to the pericardial space. One or more flexible members are inserted into and through the incision. Portions of the one or more flexible members are formed into a tubular barrier against exposed edges of the pericardium. Portions of one or both ends of the one or more flexible members are formed away from the tubular barrier and around the exposed edges of the pericardium to line at least portions of the pericardium around the incision. The one or more flexible members include a plurality of strips of flexible and lubricious material in one embodiment of the invention.

BRIEF DESCRIPTION OF THE DRAWINGS

FIGS. 10A and 10B are top views of a pericardium retractor in accordance with another embodiment of the invention in closed and open states, respectively.

FIG. 13 is a top view of a pericardium retractor in accordance with another embodiment of the invention inserted into and opened within a pericardial space.

DETAILED DESCRIPTION OF THE PREFERRED EMBODIMENTS

Figure 1A:
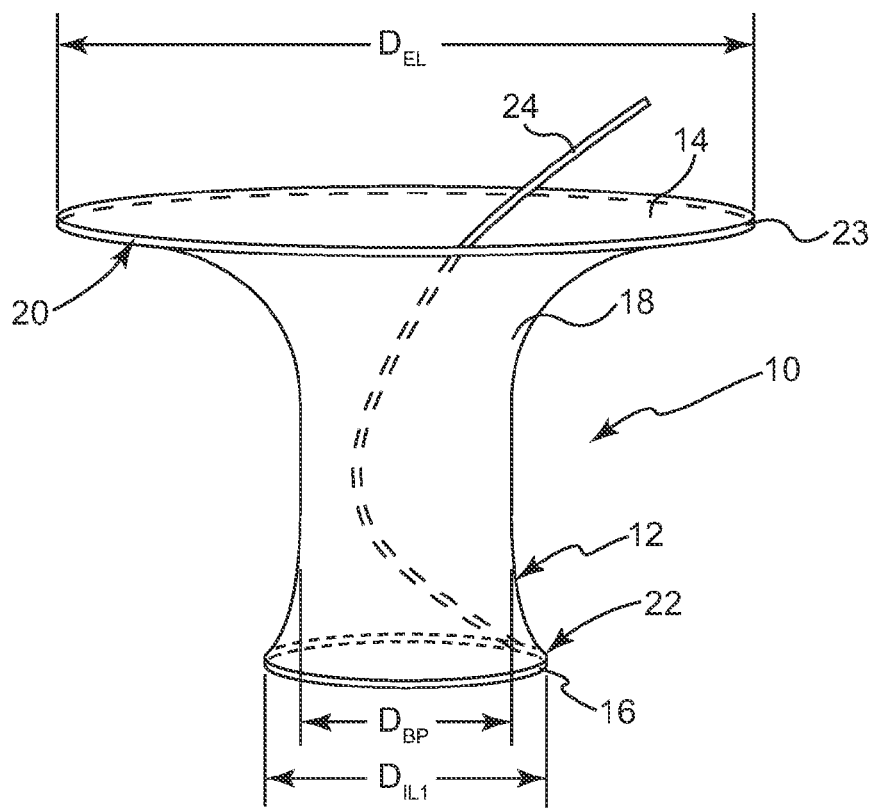
FIG. 1A is an isometric view of a pericardium management tool in accordance with one embodiment of the present invention in a retracted state.
Figure 1B:
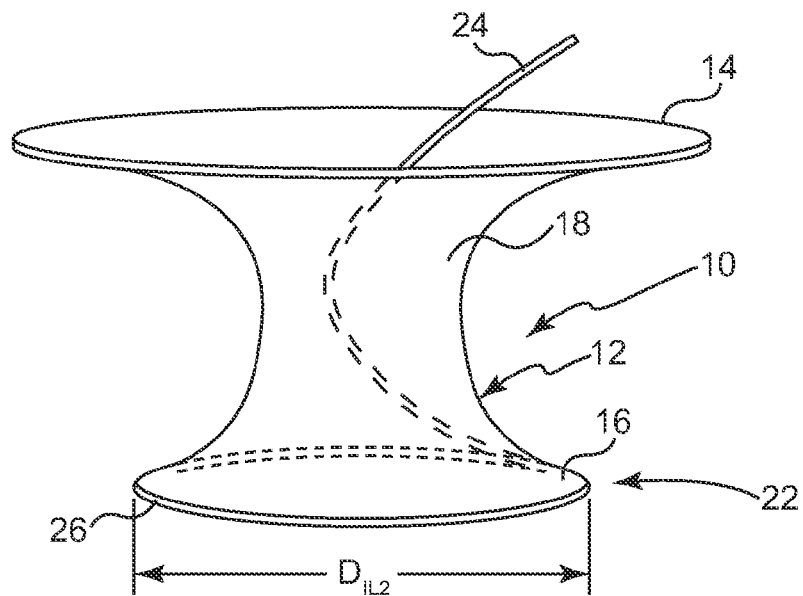
FIG. 1B is an isometric view of the pericardium management tool shown in FIG. 1A in an expanded state.

FIGS. 1A and 1B are illustrations of a pericardium management tool 10 in accordance with one embodiment of the invention. As shown, the tool 10 is a flexible member having a tubular body 12 with a first or external end 14 and a second or internal end 16. A barrier portion 18 of the body 12 between the ends 14 and 16 has a diameter $D_{BP}$. A lip 20 on the external end 14 of the body 12 has a diameter $D_{EL}$ that is greater than the diameter $D_{BP}$ of the barrier portion 18. An extendable lip 22 on the internal end 16 of the body 12 is expandable with respect to the body between a first or retracted state shown in FIG. 1A and a second or expanded state shown in FIG. 1B. In the retracted state shown in FIG. 1A, the extendable lip 22 has a diameter $D_{IL1}$ that can be greater than, less than or equal to the diameter $D_{BP}$ of the barrier portion 18. In the embodiment shown, the extendable lip structure 22 has a diameter $D_{IL1}$ in its retracted state that is slightly larger than the diameter $D_{BP}$ of the barrier portion 18. In the expanded state shown in FIG. 1B, the extendable lip structure 22 has a diameter $D_{IL2}$ that is greater than the diameter $D_{BP}$ of the barrier portion 18.

In the embodiment shown in FIGS. 1A and 1B, the entire body 12 is formed from flexible (i.e., compliant) material such as fabric manufactured of expanded PTFE threads. Material of this type is commercially available as Gore-Tex fabric from W.L. Gore. Some embodiments of the invention are formed from material that is also expandable, although other embodiments of the invention are constructed from material that is not expandable. Materials of this type can also be elastic, although other embodiments of the invention are constructed from material that is not elastic. Another characteristic of material of this type is that it has a relatively low coefficient of friction, and therefore has relatively low friction surfaces. Still other embodiments of the invention are formed from other materials (e.g., Dacron) having a lubricious coating.

In the embodiment of pericardium management tool 10 shown in FIGS. 1A and 1B, the lip 20 on the external end 14 of body 12 is fixed in size. The lip 20 can, for example, be formed by stretching the fabric around a hoop (not visible) of wire or other elongated material to form a tubular pocket 23, and forming a hem in the fabric to retain the hoop inside the tubular pocket. As shown in FIGS. 1A and 1B, in this embodiment of the tool 10, the diameter of the body 12 continuously increases between the diameter $D_{BP}$ of the barrier portion 18 and the diameter $D_{EL}$ of the external lip 20.

The extendable lip 22 is moved between its retracted and expanded states in this embodiment by a flexible elongated element such as wire 24 that is inserted into and withdrawn from a tubular pocket 26 in the internal end 16 of the body 12. Pocket 26 can be formed by folding and hemming the fabric on the end 16 of the body 12. By forcing the wire 24 in a direction generally parallel to its length into the pocket 26 through a hole (not shown), the wire is be formed into a hoop of increasing circumference and diameter that stretches the fabric of the body 12 to expand the lip 22. The lip 22 is retracted by withdrawing the wire 24 from the pocket 26.

Figure 2A:
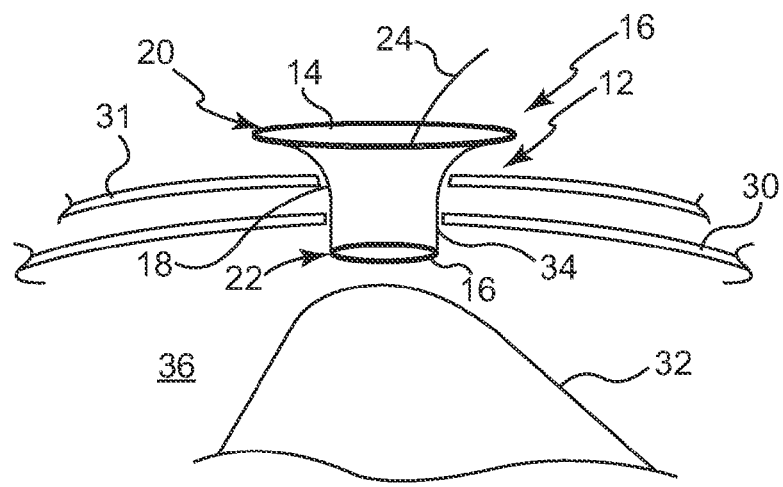
FIGS. 2A-2C are illustrations of the pericardium management tool shown in FIG. 1A being inserted into and deployed within a patient's pericardial space.
Figure 2B:
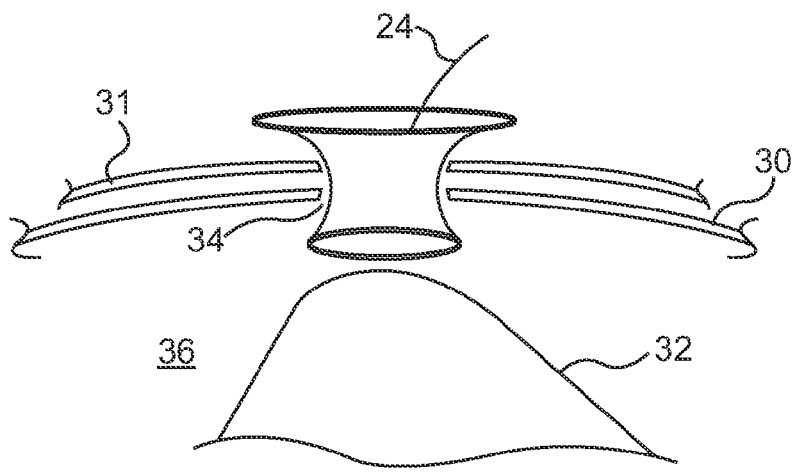
Figure 2C:
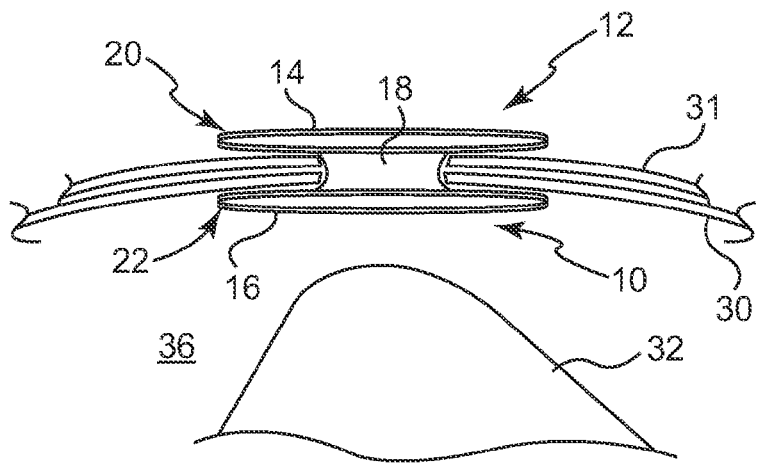

FIGS. 2A-2C illustrate a method for operating and deploying the tool 10 to manage a patient's pericardium 30 and provide access to heart 32. The pericardium 30 is accessed from a desired location through the patient's skin 31. An incision 34 is then made through the pericardium 30 to provide access to the pericardial space 36 surrounding heart 32. As shown in FIG. 2A, the internal end 16 of the body 12 is inserted through the skin 31 and incision 34, and positioned within the pericardial space 36. The lip 20 on the external end 14 of the body 12 will remain on the outside of the pericardium 30, and typically on the outside of the patient's skin 31.

The expansion of lip 22 can then be initiated by forcing the wire 24 into the pocket 26 as shown in FIG. 2B. As the wire 24 is fed into the pocket 26 the circumference and diameter of the lip 22 will expand with respect to the barrier portion 18 and draw the internal end 16 of the body 12 closer to the interior surface of pericardium 30. This expansion operation continues until the lip 22 is in its expanded state shown in FIG. 2C. When the tool 10 is deployed with the lip 22 in the expanded state, the barrier portion 18 of the body 12 forms a tubular structure around and against the exposed edges of the pericardium 30 and skin 31. The lip 22 also extends beyond the edges of the incision 34 and forces the fabric of the lip and body 12 to be positioned on or adjacent to the interior surfaces of the pericardium 30 around the incision. The lip 22 thereby covers or lines the inside surface of the pericardium 30 around the incision 34. Similarly, this deployment causes the external lip 20 to be located on or least adjacent to the external surface of the patient's skin 31, with the fabric of the external lip and body 12 extending beyond and around the opening over the external surface of the skin to form a cover or lining.

Tool 10 can be efficiently inserted and deployed. The deployed tool 10 surrounds the incision 34 in the pericardium 30 and provides a low-friction access port to the pericardial space 36. Since the edges of the pericardium 30 at the incision 34 are covered and protected, they will not interfere with surgical or other procedures being performed through the deployed tool 10. The deployed tool 10 also engages the pericardium 30 around the incision 34 to such a degree that the tool can be manipulated to lift, shift or otherwise move the location of the barrier portion 18, and therefore the access port, as desired during the surgical procedure. The surgeon can thereby effectively enhance his or her visualization of and access to the pericardial space 36 without interference from the edges of the pericardium 30. The characteristics of the tool 10 also enable the device to continually resize and conform to changes in the shape or size of the incision 34 that might be caused during the surgical procedure.

Upon completion of the surgical or other procedure the tool 10 can be removed from the incision 34. This removal can be facilitated by returning the lip 22 on the internal end 16 to its retracted state (e.g., by withdrawing the wire 24). The above described advantages of the tool 10 are thereby achieved by a device that can be efficiently removed following the completion of the procedure.

Pericardial management tools in accordance with the invention and having features and advantages such as those described above in connection with tool 10 can take other forms. By way of example, and not shown, in other embodiments of the invention the barrier portion 18 and lip 20 on external end 14 can be formed of rigid materials such as polymers. The lip 20 on the external end 14 need not be fixed, but instead can have structures such as those of the lip 22 on the internal end 16 that can be moved between retracted and expanded states. The extendable lip 22 can also be formed from different materials, including rigid materials, and different structures and methods can be used to move the lip between its retracted and expanded states. In still other embodiments, the tool includes a low friction material coating (e.g., in solid or liquid form) on the interior surfaces of the body 12 or at least on the barrier portion 18. The entire tool 10, or just portions, can be constructed from any suitable material such as, for example, fabrics, metals, polymers or biologic materials. The exterior surface of the tool 10 near the lips 20 and/or 22 can also include adhesive elements or coatings, or other tissue-engaging structures or material, that will facilitate the attachment of the lips to the adjacent tissue when the device is deployed. Although the tubular body 12 has a circular cross section in the illustrated embodiment, other embodiments (not shown) have other cross sectional shapes.

Figure 3:
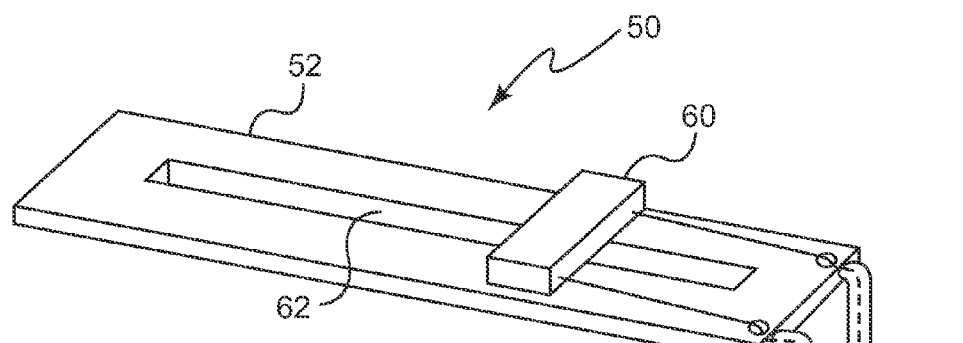
FIG. 3 is an isometric view of a device for inserting and deploying the pericardium management tool shown in FIG. 1A.
Figure 4:
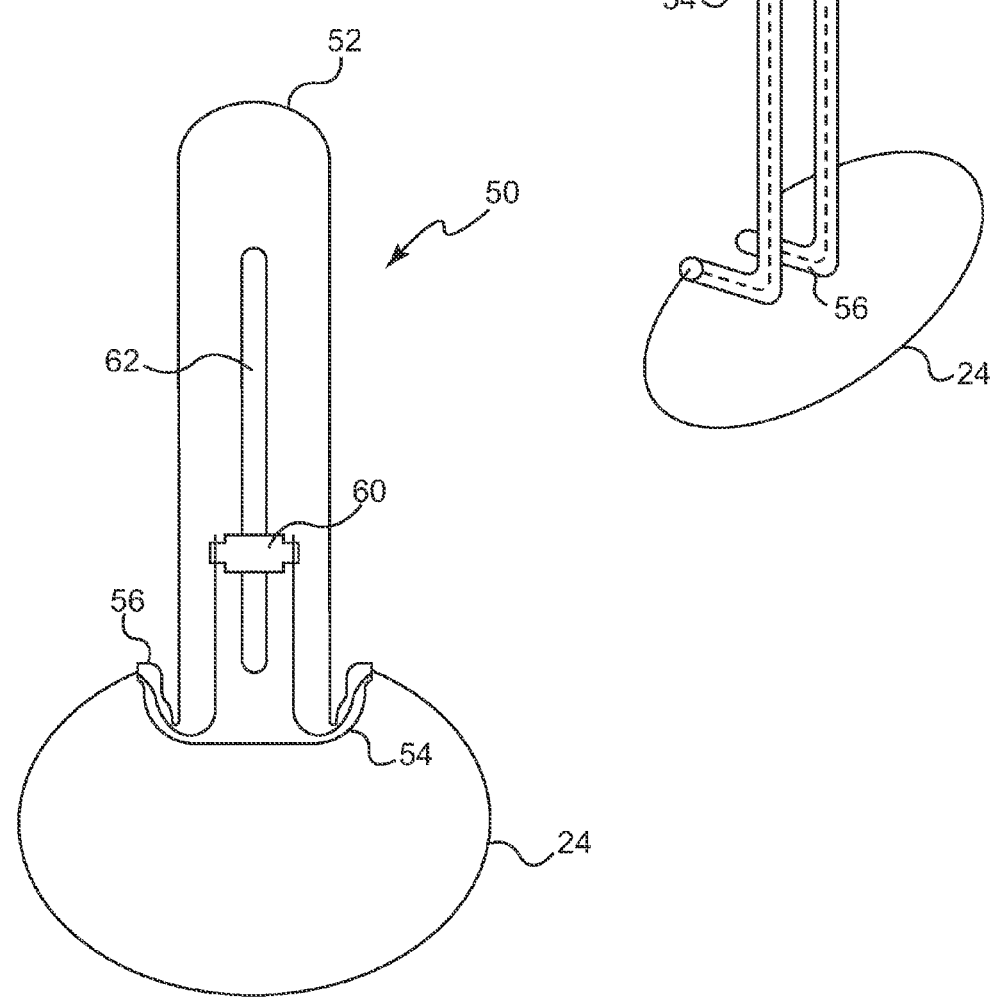
FIG. 4 is a top view of the deployment device shown in FIG. 3.

FIGS. 3 and 4 are illustrations of a deployment device 50 that can be used to insert and deploy the pericardium management tool 10. As shown, deployment device 50 has a handle 52 with a pair of guide members 54 extending from one end. The guide members 54 are tubes and have fingers 56 on the ends opposite the handle 52 that extend in a direction back toward and generally parallel to the handle. The wire 24 that is used to deploy the tool 10 (not shown in FIG. 3 or 4) extends through the guide members 54 and out the ends of the fingers 56. The portion of the wire 24 extending from the fingers 56 forms a hoop that is located in the extendable lip 22 of the tool 10 when the tool is mounted on the deployment device 50, thereby supporting the tool during its use. The ends of the wire 24 extending from the ends of the guide members 54 mounted to the handle 52 are connected to a slide 60. Slide 60 is movably mounted to the handle 52, and in the embodiment shown is mounted to a slot 62 for movement along the length of the handle. The circumference and diameter of the hoop in the wire 24 can be expanded and retracted by moving the slide 60 toward and away from the end of the handle 52 with the guide members 54, respectively.

Figure 5:
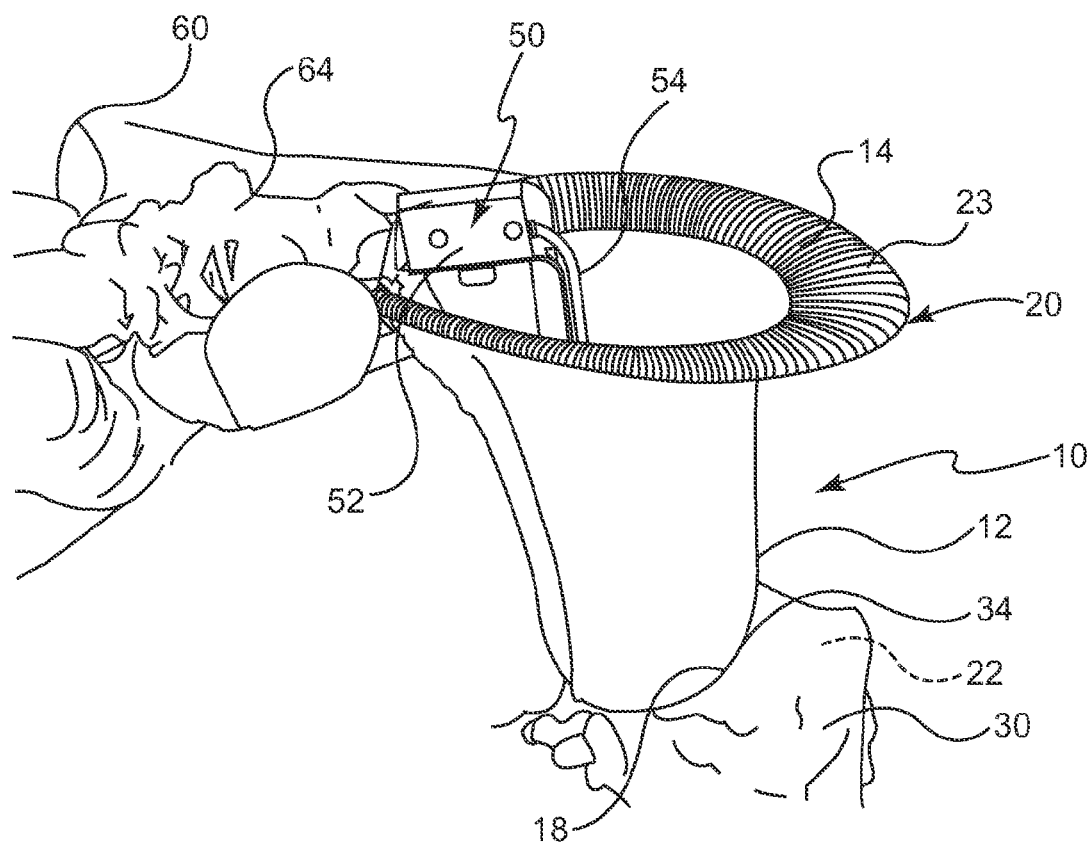
FIG. 5 is an isometric view, taken from the side, showing the pericardium management tool of FIG. 1A on the deployment device of FIG. 3, with the internal end of the tool and device inserted into and deployed with the pericardial space.
Figure 6:
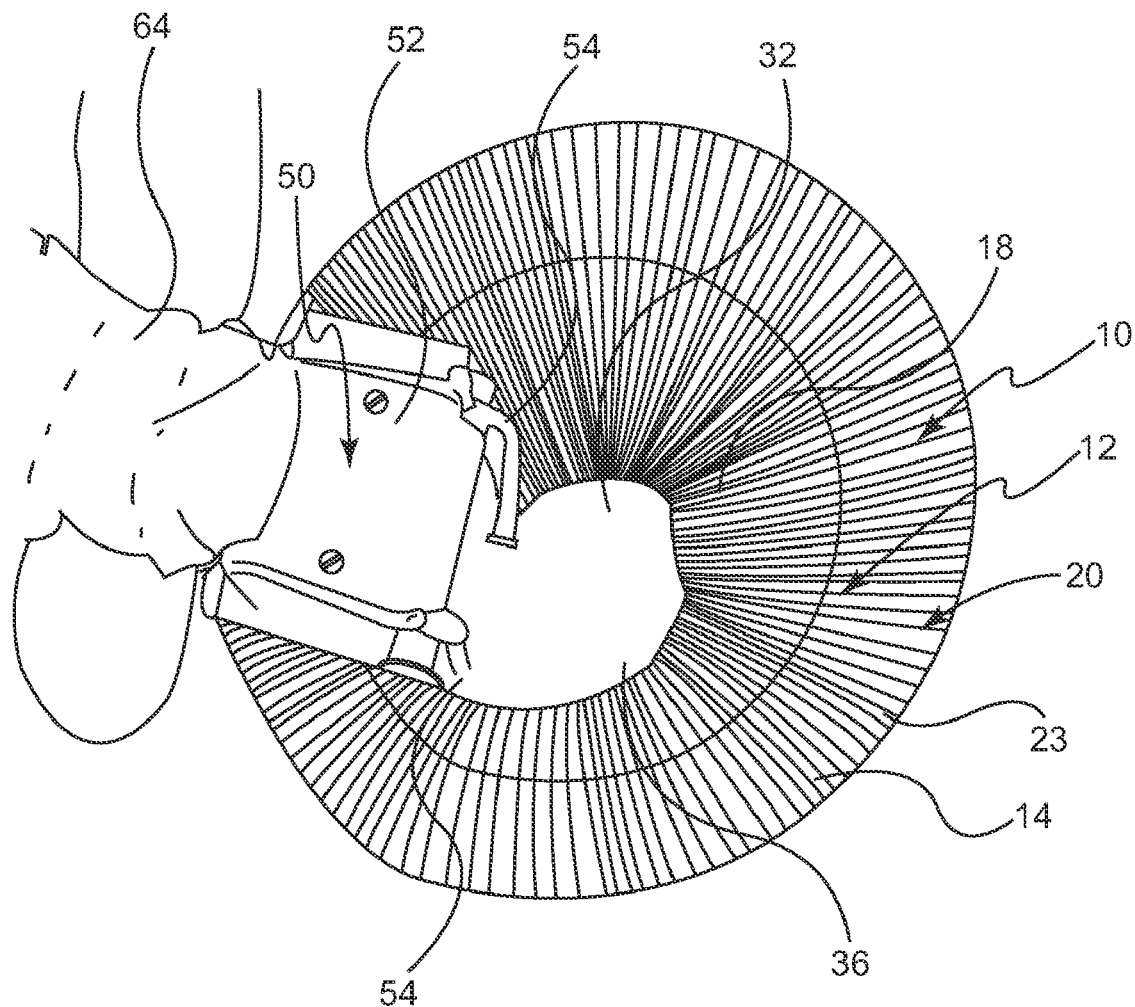
FIG. 6 is an isometric view of the deployed tool and device shown in FIG. 5.

FIGS. 5 and 6 are illustrations of the pericardium management tool 10 mounted to the deployment device 50. A cover 64 of flexible fabric encloses the portions of the deployment device 50 between the slide 60 and end portion of handle 52. The internal end 16 and extendable lip 22 of the tool 10 (not visible in FIGS. 5 and 6) are positioned through an incision 34 into mammalian pericardium 30 in these figures. The slide 60 has been actuated (e.g., by the surgeon's thumb) to drive the extendable lip 22 to its expanded state. In FIG. 6 the pericardial space 36 and heart 32 are visible through the opening in the body 12.

Figure 7:
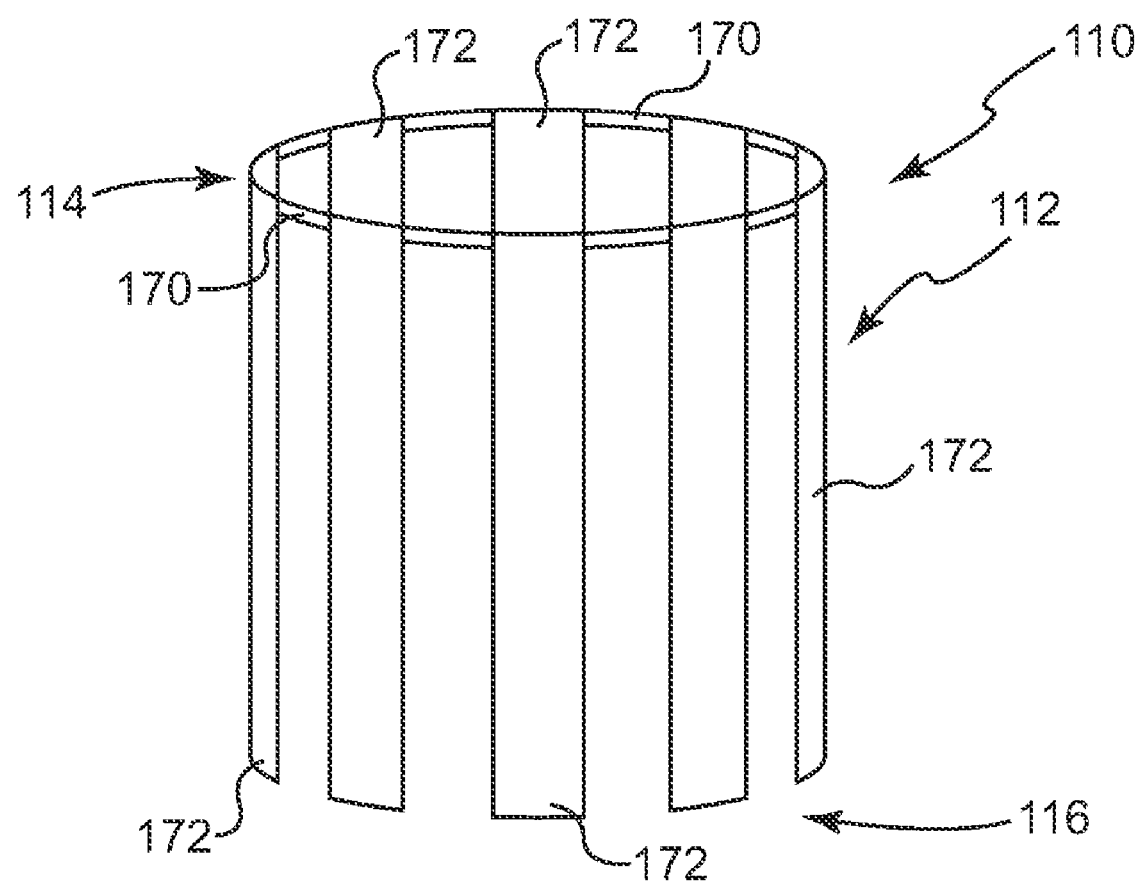
FIG. 7 is an isometric view of a pericardium management tool in accordance with another embodiment of the invention.

FIG. 7 is an illustration of a pericardium management tool 110 in accordance with another embodiment of the invention. As shown, tool 110 includes a hoop 170 and a body 112 formed by a plurality of flexible members such as material strips 172. The material strips 172 can be formed of any of the materials of the body 12 of tool 10 described above. In one embodiment, for example, strips 172 are formed of relatively low friction and flexible material such as PTFE. The strips 172 extend from the hoop at spaced apart locations and can be formed of relatively thin sheet material. Hoop 170 can be an elongated metal or polymer member (e.g., wire). Material strips 172 can be attached to the hoop 170 by wrapping the ends of the strips around the hoop and securing the ends to the hoop or adjacent portions of the strips (e.g., by a sewn hem or adhesive). The end 114 of tool 110 at which the material strips 172 are attached to the hoop 170 is an exterior end of the tool, while the free ends of the strips are at an internal end 116 of the tool.

Figure 8A:
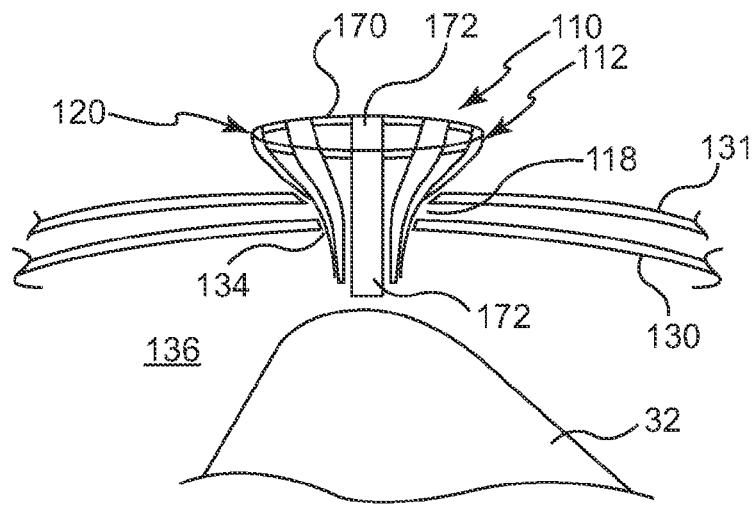
FIGS. 8A-8C are illustrations of the pericardium management tool shown in FIG. 7 being inserted into and deployed within a patient's pericardial space.
Figure 8B:
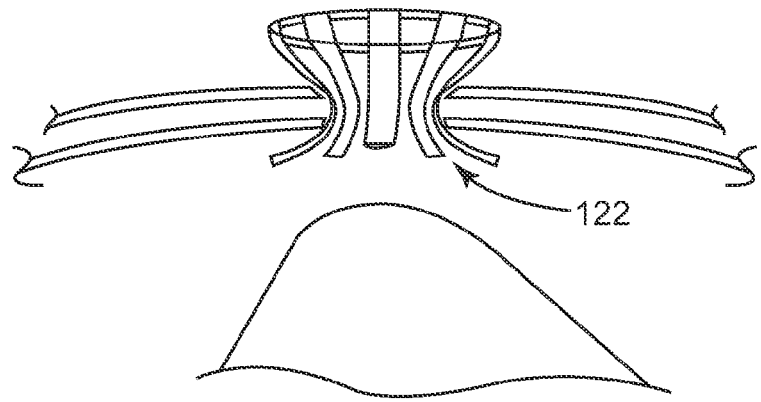

FIGS. 8A-8C and 9 illustrate a method for operating and deploying the tool 110 to manage a patient's pericardium 130 and provide access to heart 132. The pericardium 130 is accessed from a desired location through the patient's skin 131. An incision 134 is then made through the pericardium 130 to provide access to the pericardial space 136 surrounding heart 132. As shown in FIG. 8A, the portions of material strips 172 on the internal end 116 of the body 112 are inserted through the skin 131 and incision 134, and positioned within the pericardial space 136. The body 112 of the device 10 is in a retracted state during this insertion step. The hoop 170 on the external end 114 of the body 112 functions as a lip 120 and remains on the outside of the pericardium 130, and typically on the outside of the patient's skin 131.

The body 112 of tool 110 is then expanded within the pericardial space 136 by radially extending the free ends of the material strips 172 in a fanned arrangement under the pericardium 130. The portions of the material strips 172 on the internal end 116 of the body 112 are thereby expanded in diameter and circumference with respect to the diameter and circumference of a barrier portion 118 that engages the edges of the pericardium 130 at the incision 134. These steps can be done by hand (e.g., by the surgeon using his or her fingers to tuck the material strips 172 under the pericardium 130) or with the assistance of instruments. The portions of the material strips 172 on the ends 116 of the body 112 form a lip 122 under the pericardium 130. This expansion operation continues until the lip 122 is in its expanded state shown in FIG. 8C.

Figure 8C:
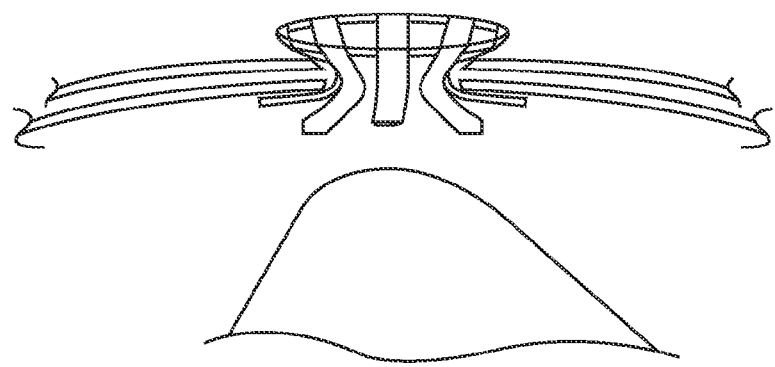
Figure 9:
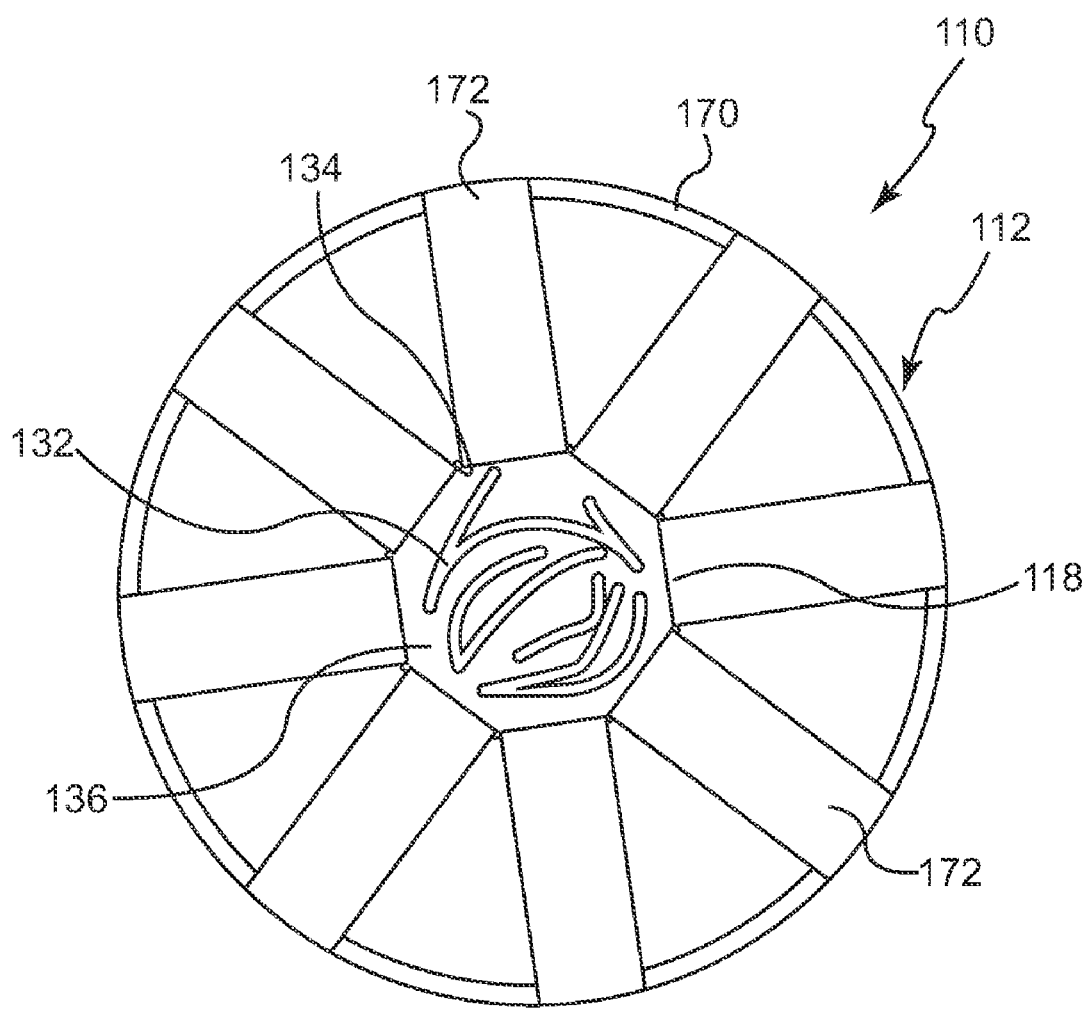
FIG. 9 is a top view of the deployed pericardium management tool shown in FIG. 7.

As perhaps best shown in FIGS. 8C and 9, when the tool 110 is deployed with the lip 122 in the expanded state, the portions of the material strips 172 at barrier portion 118 are positioned closely adjacent to one another and form a tubular structure against the exposed edges of the pericardium 130 and skin 131. In the illustrated embodiment the portions of the material strips 172 at barrier portion 118 are located immediately adjacent to one another. In other embodiments (not shown) the strips 172 can overlap one another, or be spaced from one other, at barrier portion 118.

The lip 122 extends beyond and around the edges of the incision 134 and forces the material strips 172 to be positioned on or adjacent to the interior surfaces of the pericardium 130 around the incision, thereby lining the pericardium around the incision. When deployed, the illustrated embodiment of tool 110 has gaps in the lip 122 between the material strips 172. However substantial portions of the pericardium 130 around the incision 134 are still lined by the lip 122 (e.g., sufficient portions to reduce or prevent the pericardium from interfering with the surgical procedure). Following this deployment operation the external lip 120 will typically be located on or at least adjacent to the external surface of the patient's skin 131, with the material of strips 172 at the lip 120 and body 112 extending beyond and around the opening over the external surface of the skin.

Pericardium management tool 110 can be efficiently inserted and deployed to surround the incision and provide a low-friction access port to the pericardial space 136. FIG. 9, for example, shows how the deployed tool 110 provides access to the pericardial space 136 and heart 132. The tool 110 can be removed from the incision 134 following the completion of the surgical procedure by returning the lip 122 to its retracted state and pulling the body 112 out of the incision. The functions and associated advantages provided by pericardium management tool 110 are the same or similar to those of tool 10 described above.

Pericardium management tools in accordance with the invention having features and advantages such as those described above in connection with tool 110 can take other forms. By way of example, and not shown, in other embodiments if the invention the portions of the strips 172 (e.g., flexible members) that are positioned on the outside and/or the inside of the pericardium 130 can be formed of rigid material, and the portions of the strips forming the barrier portion 118 can be formed of flexible material or have hinge structures that enable the ends to be fanned out within the pericardial space 136. Malleable metals or other material or structures can be added to the material strips 172 at the barrier portion 118 to cause the strips to retain their expanded state positions. The strips need not be formed of low friction material, but can instead be formed of other materials and have a coating of low friction material on at least those portions forming the interior surface of barrier portion 118. The material strips 172 can also be curved or otherwise shaped to reduce or eliminate the size of the gaps between the strips at the lips 120 and/or 122 when the tool 110 is deployed. Adhesive or other structures (e.g., hook and loop fasteners) on the material strips (e.g., on the edges) can be used to secure the strips to one another. Other features of the tool 10 described above can also be incorporated into tool 110.

Figure 11B:
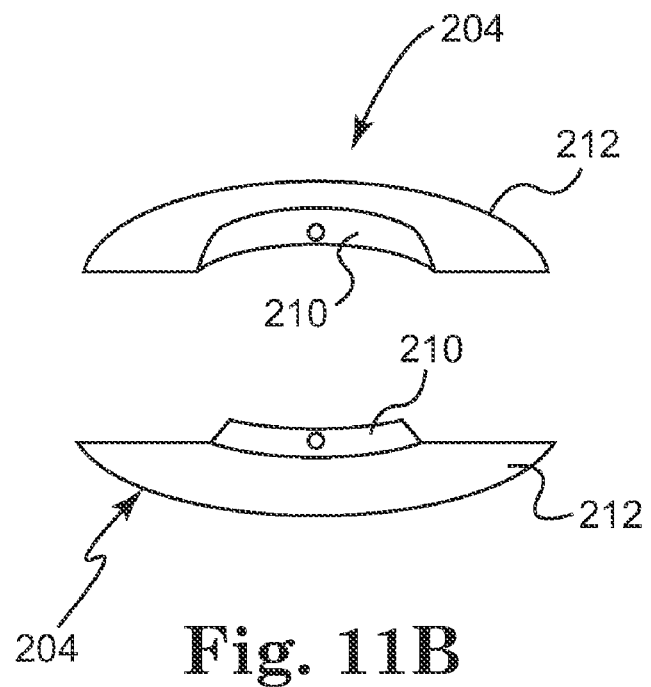
FIGS. 11A and 11B are detailed isometric views of the blades of the retractor shown in FIGS. 10A and 10B in the closed and open states, respectively.
Figure 11A:
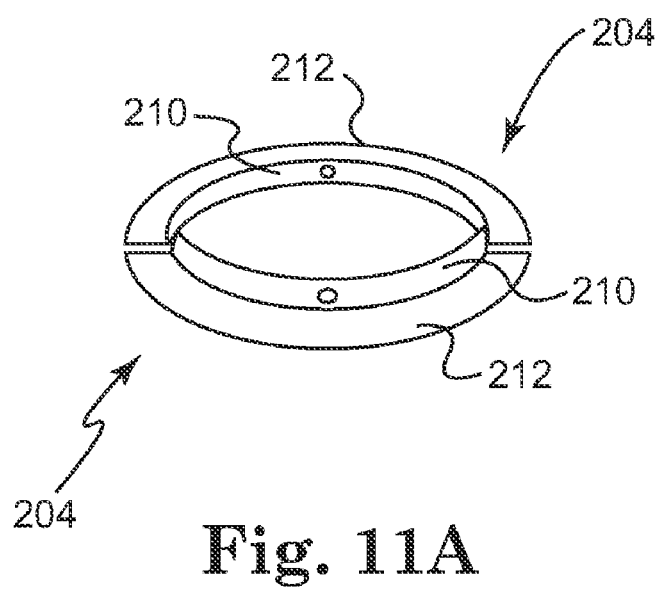

A retractor 200 in accordance with another embodiment of the invention is shown in FIGS. 10A and 10B. Retractor 200 includes a handle 202, a pair of blades 204 and an actuating member 208. Blades 204 are shown in greater detail in FIGS. 11A and 11B. The retractor 200 and blades 204 are shown in a closed or retracted position in FIGS. 10A and 11A with the blades located adjacent to one another, and in an open or extended position in FIGS. 10B and 11B with the blades spaced apart from one another.

Blades 204 each have an upright wall portion 210 and a lip 212 extending from the wall portion. Wall portions 210 have a convex surface in the embodiment shown. Similarly, in the embodiment shown the lips 212 have a convex outer edge. In other embodiments of the invention the wall portions 210 and the outer edges of the lips 212 have other shapes (e.g., are flat or straight).

Handle 202 is an elongated member in the embodiment shown and has a proximal end 214 and a distal end 216. One of the blades 204 (i.e., a fixed blade) is mounted to the distal end 216 of the handle 202 with the lip 212 facing the proximal end 214. An elongated member such as shaft 215 can mount the fixed blade 204 to the handle 202. Actuating member 208 includes a U-shaped arm 217 with a proximal end 218 movably mounted to the handle 202 and a distal end 220 mounted to the other blade 204 (i.e., the movable blade). The blade 204 is mounted to the distal end 220 of arm 217 with the lip 212 of the blade facing away from the distal end 216 of the handle 202. In the embodiment shown, the proximal end 218 of arm 217 is slidably mounted to a slot 222 in the handle 202 by an a slide 224.

Figure 12A:
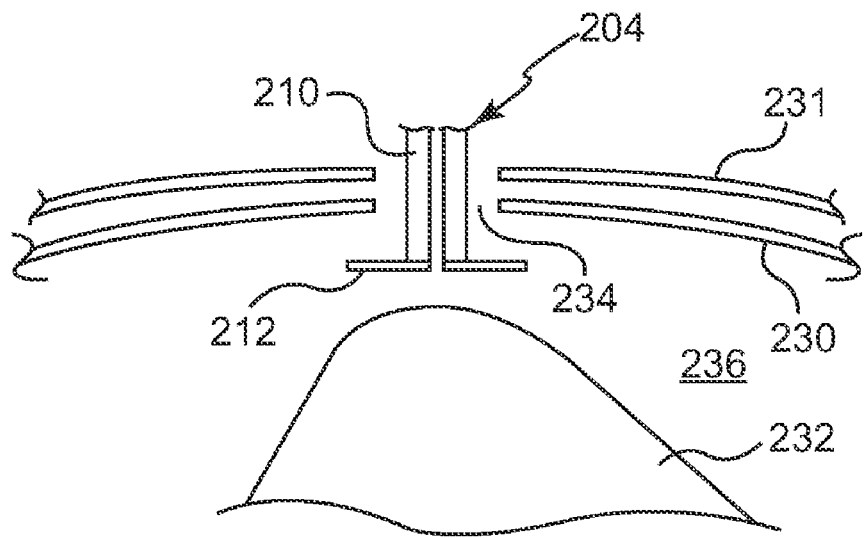
FIGS. 12A and 12B are illustrations of the retractor shown in FIGS. 10A and 10B being inserted into and opened within a patient's pericardial space.
Figure 12B:
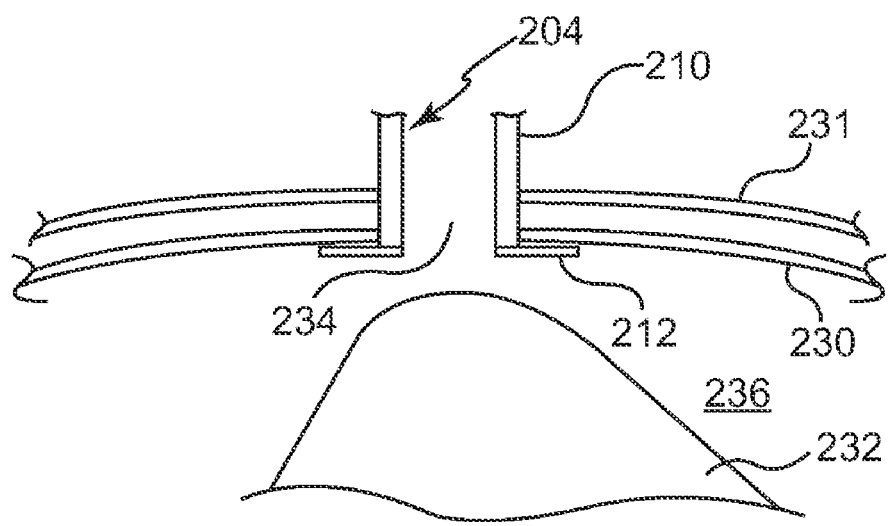

The operation of retractor 200 can be described with reference to FIGS. 10A, 10B, 11A, 11B, 12A and 12B. The pericardium 230 is accessed from a desired location through the patient's skin 231. An incision 234 is then made through the pericardium 230 to provide access to the pericardial space 236. With the handle 202 and actuating member 208 manipulated so the blades 204 are in the closed position shown in FIGS. 10A and 11A, the blades are inserted through the incision 234 to position the lips 212 within the pericardial space 236 as shown in FIG. 12A. The actuating member 208 is then actuated to move the blades 204 to the open position shown in FIGS. 10B and 11B. This expansion of the blades 204 will cause the wall portions 210 of the blades to engage the exposed edges of the pericardium 230, and the lips 212 to extend beyond the edges of the incision over the inside surface of the pericardium 230. The incision 234 is thereby spread apart, and the edges of the pericardium 230 at the incision engaged, to provide access to the pericardial space 236 and heart 232. A releasable clamp mechanism (not shown) on the handle can be used to retain the retractor 200 in the open position during surgical procedures. Upon completion of the surgical procedure the retractor 200 can be returned to its closed position and withdrawn from the incision 234.

Retractor 200 can be efficiently operated. The retractor 200 provides functions and advantages that are the same or similar to those described above in connection with tool 10. Retractor 200 can be used alone to access the pericardial space 236. Alternatively, tools such as 10 and 110 described above can be used in connection with the retractor 200 by inserting them into the opening created by the retractor.

Figure 14:
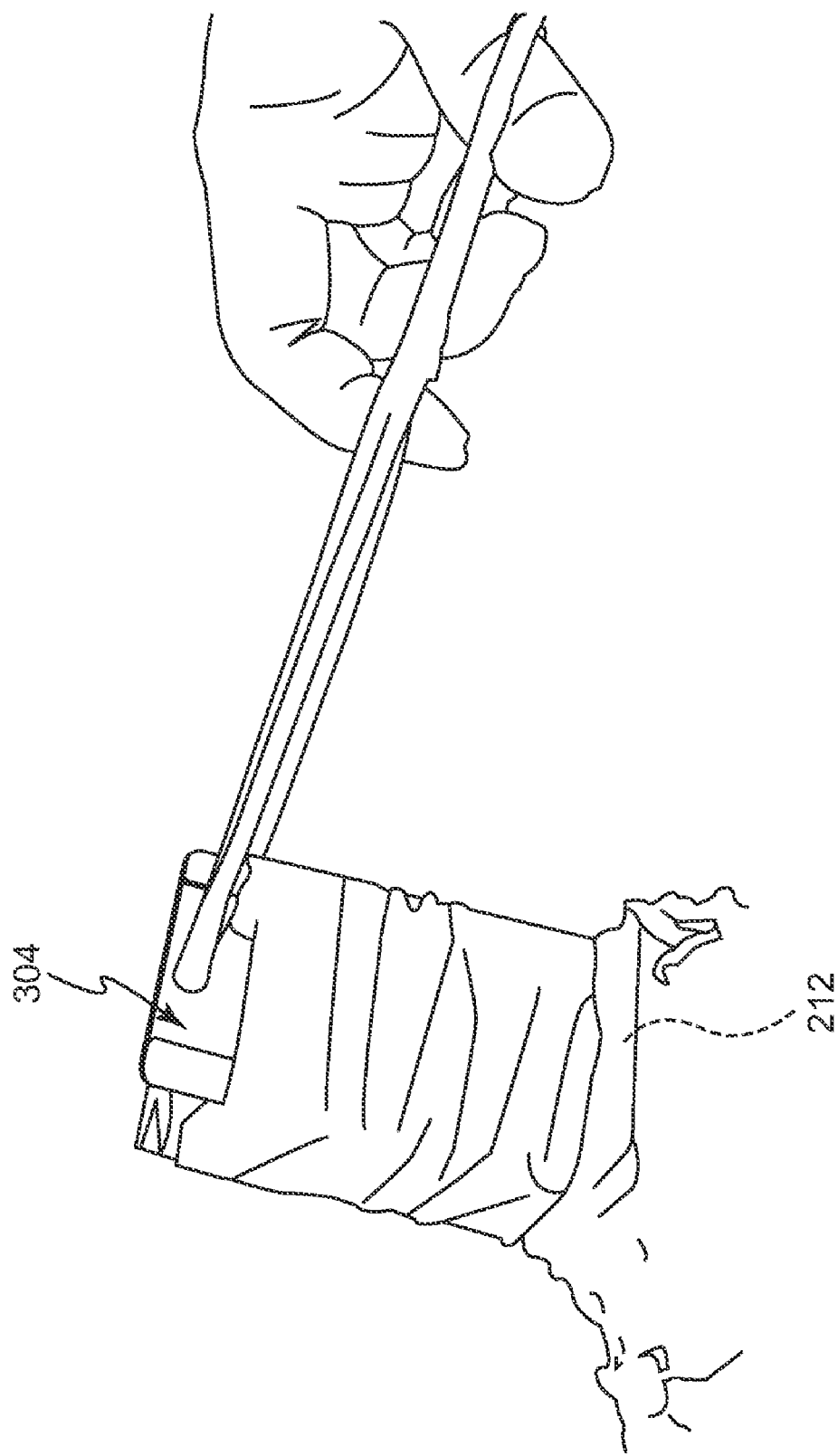
FIG. 14 is a side view of the retractor shown in FIG. 13 within the pericardial space.

FIGS. 13 and 14 are illustrations of a retractor 300 in accordance with another embodiment of the invention. In these figures the retractor 300 is shown in an open state with the blades 304 within the pericardium 330 of a mammal, exposing the pericardial space 336 and heart 332. In the embodiment shown, the actuating mechanism and handle of retractor 300 formed by a hand-held clamp mechanism 303 having a pair of arms 305 pivotally connected by a hinge 307. A releasable locking mechanism 311 is connected to the hand-engaging sections 313 of the arms 305. The blades 304 are mounted directly to the arms 305. The edges of the lips 312 are generally linear, and the wall portions 310 are generally planar. Other than these differences, retractor 300 can be substantially the same or similar to retractor 200 described above, and functions in manner that is substantially the same or similar to that of retractor 200.

Figure 16:
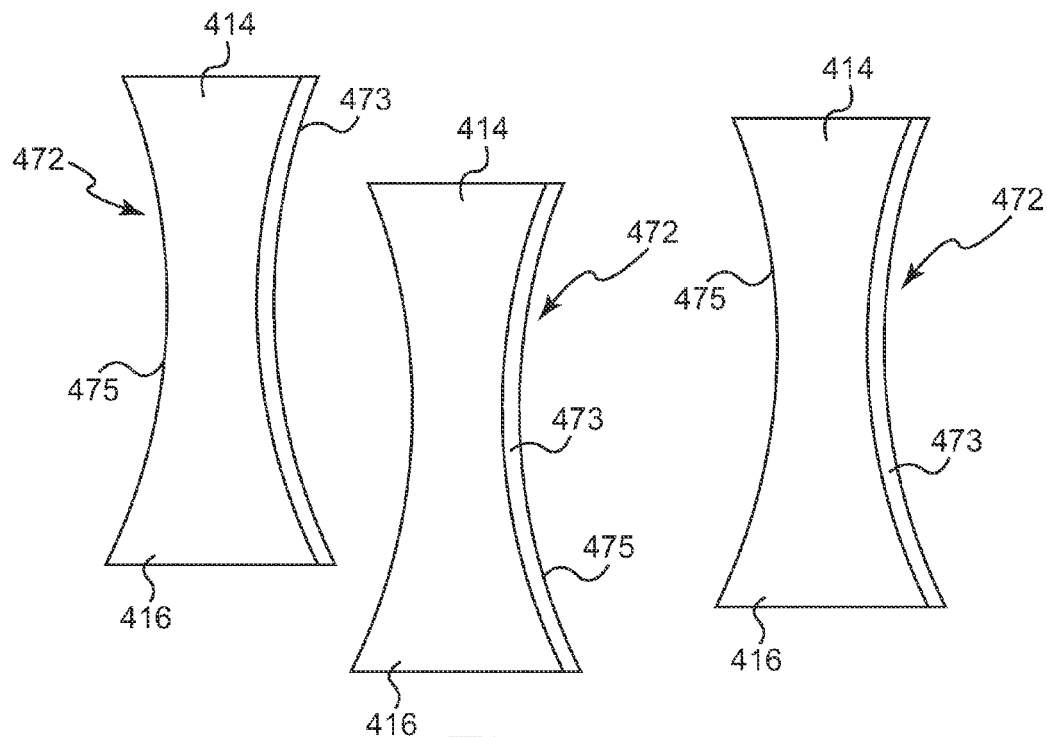
FIG. 16 is an illustration of a plurality of flexible members that can be assembled to form the tool shown in FIG. 15.
Figure 15:
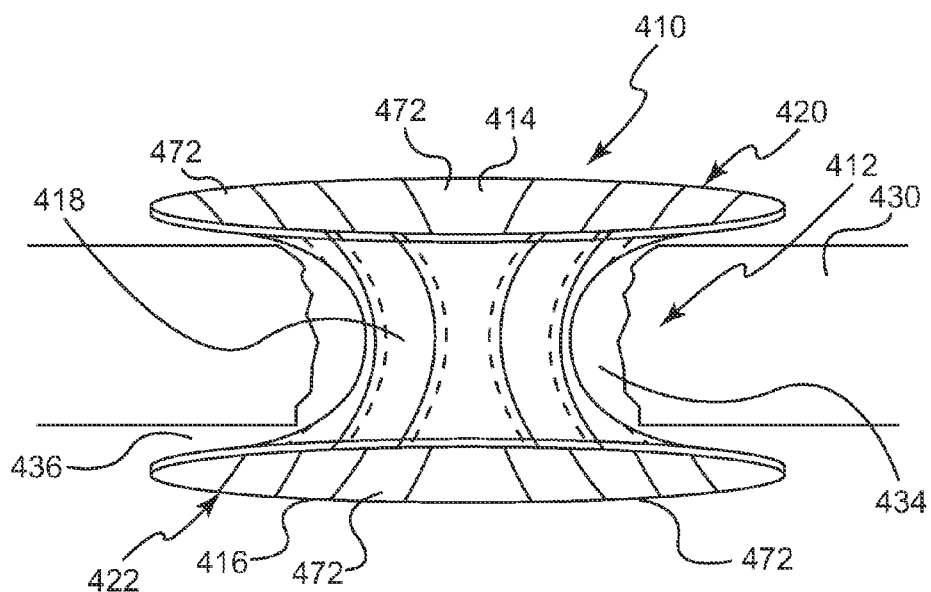
FIG. 15 is a side view of a pericardium management tool in accordance with another embodiment of the invention deployed within an incision through a patient's pericardium.

FIG. 15 is an illustration of a pericardium management tool 410 in accordance with another embodiment of the invention. Tool 410 is formed from a plurality of individual material strips 472 such as those shown in FIG. 16. Material strips 472 can be formed from any of the materials and/or structures of material strips 172 of tool 110 described above (e.g., low friction and flexible materials), and have an external end 414 and an internal end 416. In the embodiment shown, the material strips 472 are elongated members having concave side edges 475. Adhesive 473 is located on at least one side of the material strips 472 adjacent to at least one of the edges.

Tool 410 is deployed by inserting the material strips 472 individually into an incision 434 in the pericardium 430. Internal ends 416 are then tucked under the internal surface of the pericardium 430, and the external ends 414 are bent over the outside of the pericardium 430 or body. Adjacent side edges 475 of the material strips 472 can be joined together. In the embodiment shown in FIGS. 15 and 16, for example, the side edges 475 are overlapped and secured together by the adhesive 473. When deployed, the tool 410 has a tubular body 412 with a barrier portion 418 that engages and surrounds the edge of the pericardium 430 at the incision 434. The internal ends 416 of the material strips 472 are extended from retracted positions to form an extendable lip 422 that lines the interior surface of the pericardium 430 around the incision 434. The external ends 414 form a lip 420 on the outside surface of the pericardium 430 or body.

Pericardium management tool 410 can be efficiently inserted and deployed to surround the incision 434 and provide a low-friction access port to the pericardial space 436. The tool 410 can be removed from the incision 434 following the completion of the intra-pericardial procedure by pulling the body 412 out of the incision. The functions and advantages provided by pericardial management tool 410 are the same or similar to those of tools 10 and 110 described above.

Figure 17:
FIG. 17 is a sectional view of an alternative version of one of the flexible members shown in FIG. 16.
Figure 18:
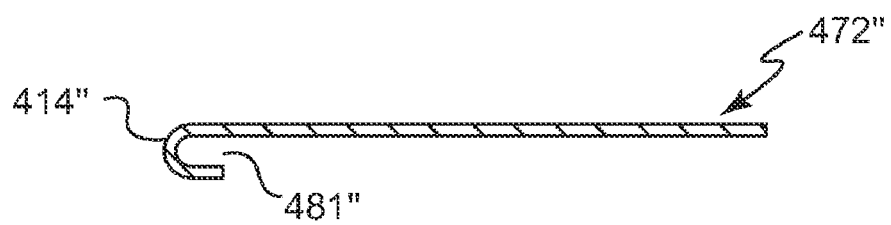
FIG. 18 is a sectional view of another alternative version of one of the flexible members shown in FIG. 16.
Figure 19:
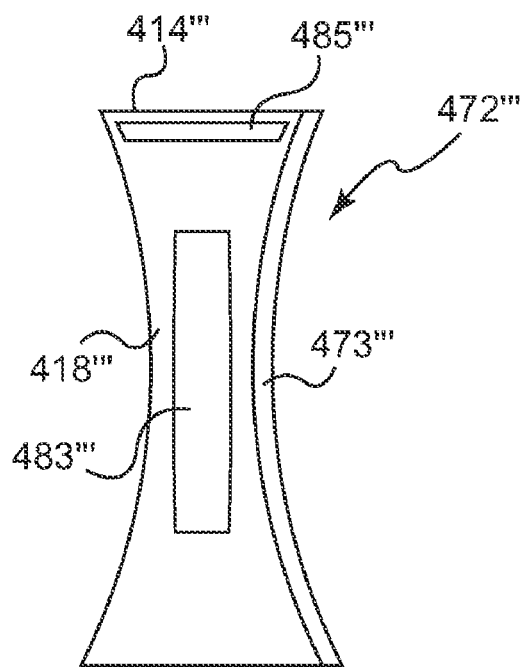
FIG. 19 is a side view of yet another alternative version of one of the flexible members shown in FIG. 16.

Pericardium management tools in accordance with the invention having features and advantages such as those described above in connection with tool 410 can take other forms. By way of example, FIG. 17 illustrates a cross section of a material strip 472' having an arcuate cross section. The actuate cross section of material strip 472' provides the strip with beam strength, and enhances the its ability to be deployed as part of the tool. FIG. 18 illustrates the external end 414" of a material strip 472". As shown, the end 414" includes an engagement structure such as pocket 481" that can be engaged by an instrument or other tool during the deployment of the tool. FIG. 19 illustrates a material strip 472'" having a tissue-engaging structure such as adhesive strip 485'" on its external end 414' and a malleable material strip 483'" adjacent the barrier portion 418'. Adhesive strip 485'" can be used to enhance the engagement of the end 414'" with the pericardium (not shown) when deployed as part of the tool in the manner described above. Malleable material strip 483'" can help the material strip 472" retain its shape when deployed as part of the tool, yet allow the material strip to be returned to other shapes during the removal of the tool. Of course the features of the material strips shown in FIGS. 17-19 can be combined with one another and with the features of the material strips 472 described above. Similarly, features of the tools 10 and 110 described above can be incorporated into material strips 472 and tool 410. Other structures such as snaps, magnets or hook and loop fasteners can be used as alternatives to the adhesive 473 to secure the material strips 472 to one another. The material strips 472 can have side edges with straight or other shape profiles, and need not be configured to engage adjacent material strips along their entire lengths. A plurality of the material strips 472 can be distributed together as a kit for assembling the tool. For example, in one embodiment (not shown) a plurality of the material strips 472 are packaged together as a kit for this purpose.

Although the present invention has been described with reference to preferred embodiments, those skilled in the art will recognize that changes can be made in form and detail without departing from the spirit and scope of the invention. For example, although not shown, tools and methods in accordance with the invention can be incorporated into delivery tools for cardiac support devices.

What is claimed is:

1. A method for managing a patient's pericardium during an intra-pericardial procedure, including:
   making an incision though the pericardium to provide access to the pericardial space;
   inserting a plurality of strips into and through the incision, each of the plurality of strips formed from a thin sheet of flexible material and having an internal end internal to the incision and a malleable metal embedded therein and capable of being deformed and self-retaining a deformed state;
   circumferentially spacing the plurality of strips around the incision immediately adjacent or overlapping each other to form a barrier with the plurality of strips engaging exposed edges of the pericardium; and
   radially extending the internal ends of the strips to a radially extended fanned arrangement around the exposed edges of the pericardium to form a lip inside the incision and line the incision, wherein the malleable metal causes the strips to retain the radially extended fanned arrangement of the internal ends of the strips.

2. The method of claim 1 wherein forming a lip inside the incision includes forming a lip within the pericardial space and under the pericardium.

3. The method of claim 1 wherein inserting the strips into and through the incision includes inserting strips extending from circumferentially spaced locations around a hoop into the incision.

4. The method of claim 3 wherein inserting the strips into and through the incision includes inserting the strips within the pericardial space and extending the internal ends of the strips under the pericardium.

5. The method of claim 4 wherein inserting the strips into and through the incision includes inserting material having a relatively low friction surface.

6. The method of claim 1 and further including attaching at least portions of the strips to one another.

7. The method of claim 1 wherein inserting the strips into and through the incision includes inserting relatively low friction strips.

8. The method of claim 1 wherein radially extending the internal ends of the strips includes increasing a diameter of the fanned arrangement with respect to a diameter of the barrier.

* * * * *